US012222270B2

(12) United States Patent
Calleri

(10) Patent No.: US 12,222,270 B2
(45) Date of Patent: Feb. 11, 2025

(54) RHEOMETER FOR DRILLING-MUD VISCOSITY MEASUREMENTS

(71) Applicant: Geolog S.r.l., San Giuliano Milanese (IT)

(72) Inventor: Antonio Calleri, San Giuliano Milanese (IT)

(73) Assignee: Geolog S.r.l., Milan (IT)

( * ) Notice: Subject to any disclaimer, the term of this patent is extended or adjusted under 35 U.S.C. 154(b) by 0 days.

(21) Appl. No.: 17/693,360

(22) Filed: Mar. 13, 2022

(65) Prior Publication Data

US 2022/0291107 A1    Sep. 15, 2022

(30) Foreign Application Priority Data

Mar. 15, 2021    (IT) .......................... 102021000006032

(51) Int. Cl.
| | | |
|---|---|---|
| *G01N 11/14* | (2006.01) | |
| *E21B 21/01* | (2006.01) | |
| *G01N 33/28* | (2006.01) | |

(52) U.S. Cl.
CPC .............. *G01N 11/14* (2013.01); *E21B 21/01* (2013.01); *G01N 33/2823* (2013.01)

(58) Field of Classification Search
CPC ..... G01N 11/14; G01N 33/2823; E21B 21/01
See application file for complete search history.

(56) References Cited

U.S. PATENT DOCUMENTS

| | | | | |
|---|---|---|---|---|
| 3,229,506 A | * | 1/1966 | Bruss | G01N 11/08 73/54.32 |
| 4,472,063 A | * | 9/1984 | Eickelmann | B01F 27/114 366/310 |
| 8,337,758 B2 | * | 12/2012 | Aymard | G09B 23/32 422/111 |
| 2010/0004890 A1 | | 1/2010 | Tonmukayakul et al. | |
| 2011/0185795 A1 | * | 8/2011 | Colquhoun | G01N 11/04 73/152.21 |

(Continued)

FOREIGN PATENT DOCUMENTS

| | | |
|---|---|---|
| CN | 205580847 | 9/2016 |
| WO | WO 2016/191119 | 12/2016 |

OTHER PUBLICATIONS

Badino Jr., A. C., Facciotti, M. C. R., & Schmidell, W.. (1997). Construction and Operation of an Impeller Rheometer for On-Line Rheological Characterization of Non-Newtonian Fermentation Broths. Brazilian Journal of Chemical Engineering, 14(4)https://doi.org/10. 1590/S0104-66321997000400010 (Year: 1997).*

(Continued)

*Primary Examiner* — Kristina M Deherrera
*Assistant Examiner* — Jean F Morello

(57) ABSTRACT

Described herein is a rheometer comprising a rotor comprising a rotary shaft and at least two screws extending longitudinally along a first portion of said shaft; a motor coupled to said shaft and adapted to rotatably drive said rotor; a stator having a cylindrical shape and adapted to contain a fluid; wherein said at least two screws form a cylindrical twin helix; wherein said cylindrical twin helix has an inside radius of 2 mm to 10 mm and an outside radius of 10 to 20 mm; wherein said stator has a radius which is longer than the outside radius of said cylindrical twin helix.

11 Claims, 4 Drawing Sheets

(56) References Cited

U.S. PATENT DOCUMENTS

2013/0086979 A1    4/2013   Samaniuk et al.
2021/0063294 A1*   3/2021   Ye .................... E21B 21/062

OTHER PUBLICATIONS

Bbosa, Ben & DelleCase, Emmanuel & Volk, Michael & Ozbayoglu, Evren. (2016). Development of a mixer-viscometer for studying rheological behavior of settling and non-settling slurries. Journal of Petroleum Exploration and Production Technology. 7. 10.1007/s13202-016-0270-6. (Year: 2016).*

Science Learning Hub ("Non-Newtonian Fluids", https://www.sciencelearn.org.nz/resources/1502-non-newtonian-fluids; accessed Mar. 22, 2024 (Year: 2010).*

Elsey "Newtonian vs. Non-Newtonian Fluids", https://www.pumpsandsystems.com/newtonian-vs-non-newtonian-fluids accessed Mar. 22, 2024 (Year: 2018).*

Rapporto di Ricerca e l'Opinione Scritta [Search Report and Written Opinion] Dated Dec. 9, 2021 From the Ministero Dello Sviluppo Economico, Direzione Generale Sviluppo Produttivo e Competitivita, Ufficio Italiano Brevetti e Marchi Re. Application No. IT202100006032. (16 Pages).

* cited by examiner

RHEOMETER FOR DRILLING-MUD VISCOSITY MEASUREMENTS

RELATED APPLICATION

This application claims the benefit of priority of Italian Patent Application No. 102021000006032 filed on Mar. 15, 2021, the contents of which are incorporated herein by reference in their entirety.

FIELD AND BACKGROUND OF THE INVENTION

The present invention relates, in general, to the field of rheometers. In particular, the present invention concerns a rheometer for measuring the viscosity of concentrated suspensions of large particles.

As is known, the rheology of suspensions containing large particles is important in many industrial application. In the oil and gas industry, for example, viscosity measurements have to be taken on drilling muds that may carry debris, also known as "cuttings".

Measuring the viscosity of such drilling muds, which are complex and heterogeneous fluids, is a difficult task, especially because of two characteristics:
distribution of cuttings of different sizes within the mud; and
sedimentation of such cuttings.

The Applicant has observed that the rotational rheometry techniques currently known in the art are not suitable for measuring the viscosity of such drilling muds.

In fact, disadvantageously, standard rotational rheometry (i.e. rotational rheometry using, for example, plate-plate or plate-cone geometries or coaxial cylinders) has centrifugal effects that lead to flow sedimentation and instability phenomena when applied to samples of drilling mud containing cuttings. For example, considering a rheometer with coaxial cylinders, such a rheometer will not be able to take measurements on dispersions containing solid particles and/or cuttings with a diameter greater than or equal to $\frac{1}{50}$th of the distance between the external surface of the rotor and the wall of the cylindrical container (such distance being commonly referred to as gap).

SUMMARY OF THE INVENTION

It is the object of the present invention to provide a rheometer that overcomes the above-mentioned problems.

In particular, it is the object of the present invention to provide a rheometer that allows measuring the viscosity of a sample of drilling mud containing cuttings.

More specifically, the present invention provides a rheometer comprising:
  a rotor comprising a rotary shaft and at least two screws extending longitudinally along a first portion of said shaft;
  a motor coupled to said shaft and adapted to rotatably drive said rotor;
  a stator having a cylindrical shape, adapted to contain a fluid;
  wherein said at least two screws form a cylindrical twin helix;
  wherein said cylindrical twin helix has an inside radius of 2 mm to 10 mm and an outside radius of 10 mm to 20 mm;
  wherein said stator has a radius which is longer than the outside radius of said cylindrical twin helix.

Preferably, said at least two screws are mutually congruent.

Preferably, said cylindrical twin helix extends longitudinally over a length of 80 mm to 120 mm.

Preferably, said cylindrical twin helix has a pitch that equals its length.

According to one embodiment, said rotary shaft has a pointed end; wherein said end has a tip angle (a) of 120° to 140°.

Preferably, said first portion of said rotary shaft has a reduced radius.

According to a particularly preferred embodiment, said stator further comprises a thermally insulating sleeve, associated with a temperature control (cooling and/or heating) and recirculation system.

These and other objects are achieved through the device as described in the appended claims, which are an integral part of the present description.

BRIEF DESCRIPTION OF THE SEVERAL VIEWS OF THE DRAWINGS

The invention will become more apparent in the light of the following detailed description, provided merely by way of non-limiting example, wherein reference will be made to the annexed drawings, wherein.

In the drawings, identical reference numerals and letters identify the same or functionally equivalent parts.

Figure 1:
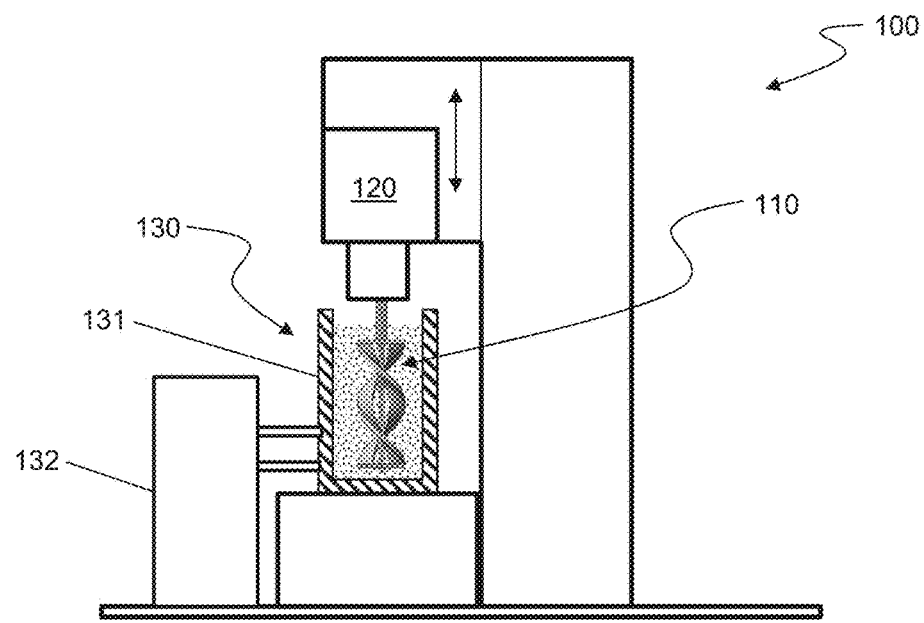
FIG. 1 is a simplified block diagram of a rheometer according to the present invention.

The drawings are not in scale.

DESCRIPTION OF SPECIFIC EMBODIMENTS OF THE INVENTION

In the following, a rheometer according to the present invention is designated as a whole by reference numeral 100.

The principle of operation of a rheometer is known and will not therefore be described in detail herein.

Figure 2:
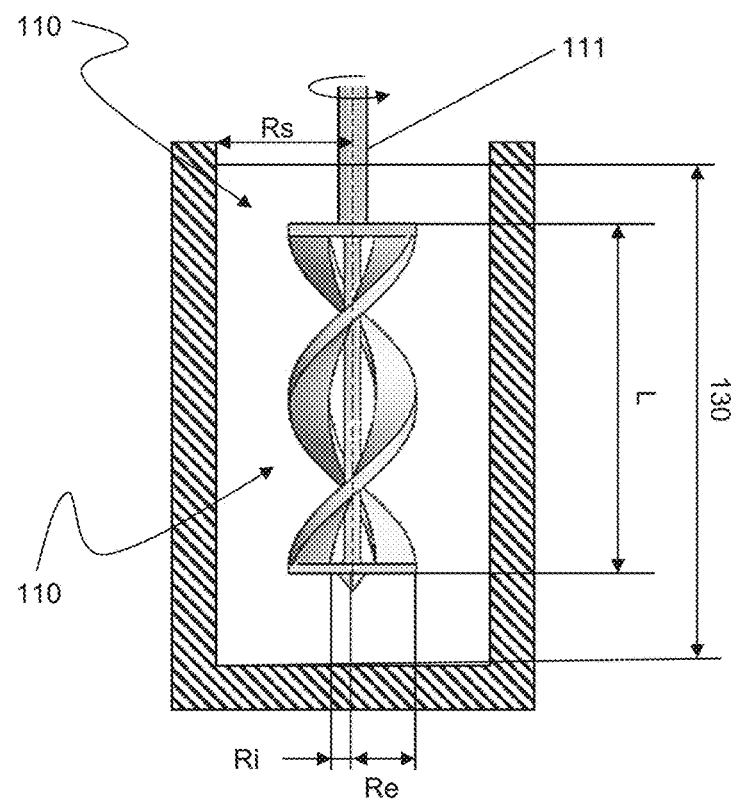
FIG. 2 shows a detail of the diagram of FIG. 3.

As shown in FIGS. 1 and 2, the rheometer 100 comprises a rotor 110.

In particular, the rotor 110 comprises a rotary shaft 111 and at least two screws 112a, 112b. Such screws 112a, 112b extend longitudinally along a first portion 111a of said rotary shaft 111.

Preferably, the first portion 111a of the shaft 111 has a reduced radius.

The rheometer 100 comprises a motor 120. The motor 120 is coupled to the shaft 111 and is adapted to rotatably drive the rotor 110 about the longitudinal axis of the rotary shaft.

Preferably, the motor 120 is connected to a control unit (not shown) that permits varying the revolution speed of the motor 120.

The rheometer 100 comprises a stator 130. The stator 130 has a cylindrical shape and is adapted to contain a fluid.

For example, the stator 130 is a cylindrical container adapted to contain the drilling mud to be analyzed.

Figure 3:
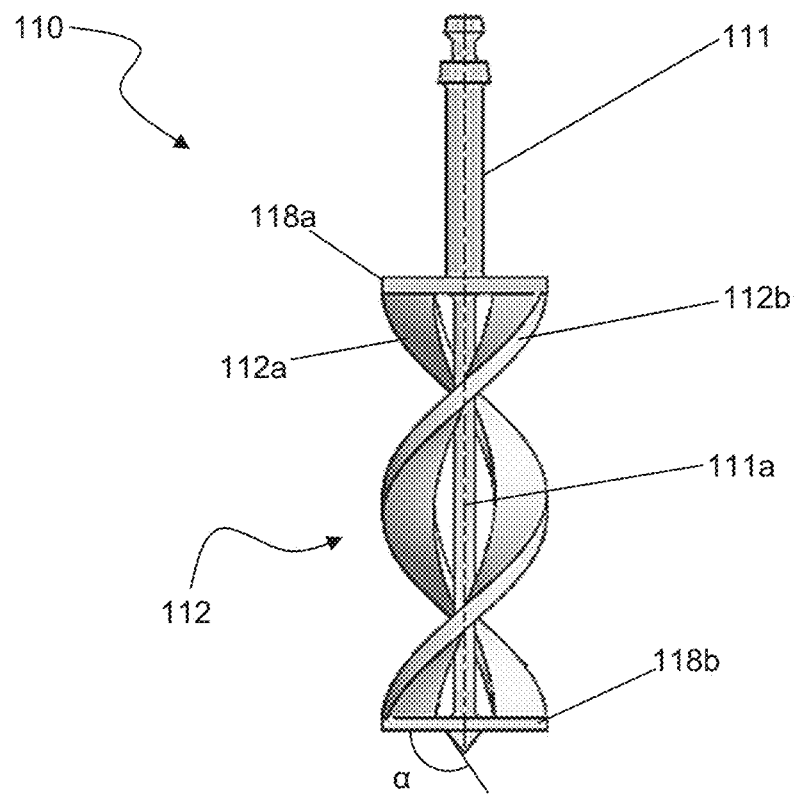
FIG. 3 is a side view of a rotor according to the present invention.
Figure 4:
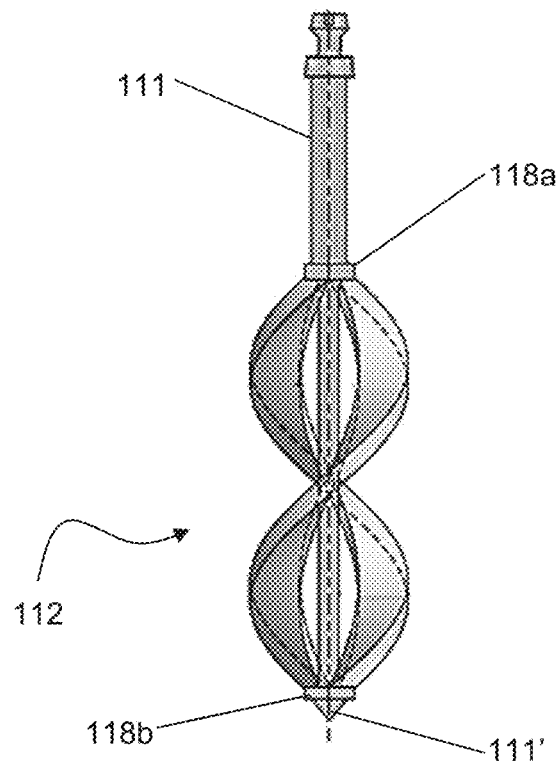
FIG. 4 is a side view along plane A-A of the rotor of FIG. 1.

With reference to FIGS. 2, 3 and 4, according to the present invention, the at least two screws 112a, 112b form a cylindrical twin helix 112.

In particular, said cylindrical twin helix 112 has an inside radius Ri of 2 mm to 10 mm and an outside radius Re of 10 mm to 20 mm.

Preferably, each screw 112a, 112b has a thickness (i.e. the difference between the inside radius Ri and the outside radius Re) of 1 mm to 10 mm, more preferably 2 mm to 8 mmm, even more preferably 4 mm to 6 mm.

For example, according to a particularly preferred embodiment, each screw 112a, 112b has a thickness of 4 mm.

In particular, as visible in FIGS. 3 and 4, the cylindrical twin helix 112 is coupled to the shaft 111 by means of two arms 118a, 118b. Such arms 118a, 118b extend perpendicularly from the shaft 111. Preferably, the cylindrical twin helix 112 is coupled to the shaft 111 by means of two arms 118a, 118b fixed to the respective ends of the at least two screws 112a, 112b.

It should be noted that this creates an empty space between the rotary shaft 111 and the cylindrical twin helix 112. In particular, said empty space has a substantially cylindrical shape. Such substantially cylindrical shape has an outer cylindrical surface defined by the rotation of the radially inner profile of the screws 112a, 112b (i.e., the radially inner profile of the cylindrical twin helix 112). Preferably, the rotation axis of the shaft 111 coincides with the longitudinal development axis of said empty space. Even more particularly, said cylindrical shaped empty space is preferably continuous from the bottom arm 118b to the top arm 118a, along a direction parallel to the shaft 111 (FIG. 4).

The stator 130 has an inside radius Rs which is longer than the outside radius Re of the cylindrical twin helix 112.

In other words, the stator 130 has such a radius Rs that allows the cylindrical twin helix 112 to be inserted therein. Preferably, the cylindrical twin helix 112 is inserted in the stator 130 in a manner such that the axis of rotation of the rotor 110 coincides with the axis of longitudinal development of the stator 130.

Preferably, the stator 130 is a cylindrical container made of steel.

Preferably, the rotor 110 is made of steel.

When measuring the rheologic parameters of a drilling mud—i.e. when the cylindrical twin helix 112 is positioned within the stator 130 and rotatably driven by the motor 120—said cylindrical twin helix 112 causes a rotational and convective motion of the drilling mud. Advantageously, such rotational and convective motion keeps the drilling mud in a homogeneous condition throughout the time of measurement, thus preventing the cuttings from sedimenting.

Preferably, the screws 112a, 112b of the cylindrical twin helix 112 are mutually congruent.

Preferably, the cylindrical twin helix 112 extends longitudinally over a length L of 80 mm to 120 mm.

Preferably, the cylindrical twin helix 112 has a pitch that equals its length L. In other words, the minimum distance between two distinct points of the helix on the same vertical equals the length L of the cylindrical twin helix 112.

Preferably, the shaft 111 has a pointed end 111'. In particular, said end has a tip angle α of 120° to 140°.

According to the present invention, the stator 130 preferably comprises a thermally insulating sleeve 131 associated with a temperature control and recirculation system 132. In particular, the stator 130 is a cylindrical container equipped with a thermally insulating sleeve 131 associated with a temperature control and recirculation system 132.

Said thermally insulating sleeve 131 and said temperature control and recirculation system 132 make it possible to keep the drilling mud at a desired constant temperature while using the rheometer 100.

For example, the thermally insulating sleeve 131 and the temperature control and recirculation system 132 allow dissipating the heat of, or heating, the stator 130 through the circulation of a thermovector fluid in proximity to the surface of the stator 130. For example, the thermovector fluid may be oil or water or any fluid normally employed for temperature control purposes.

Figure 5:
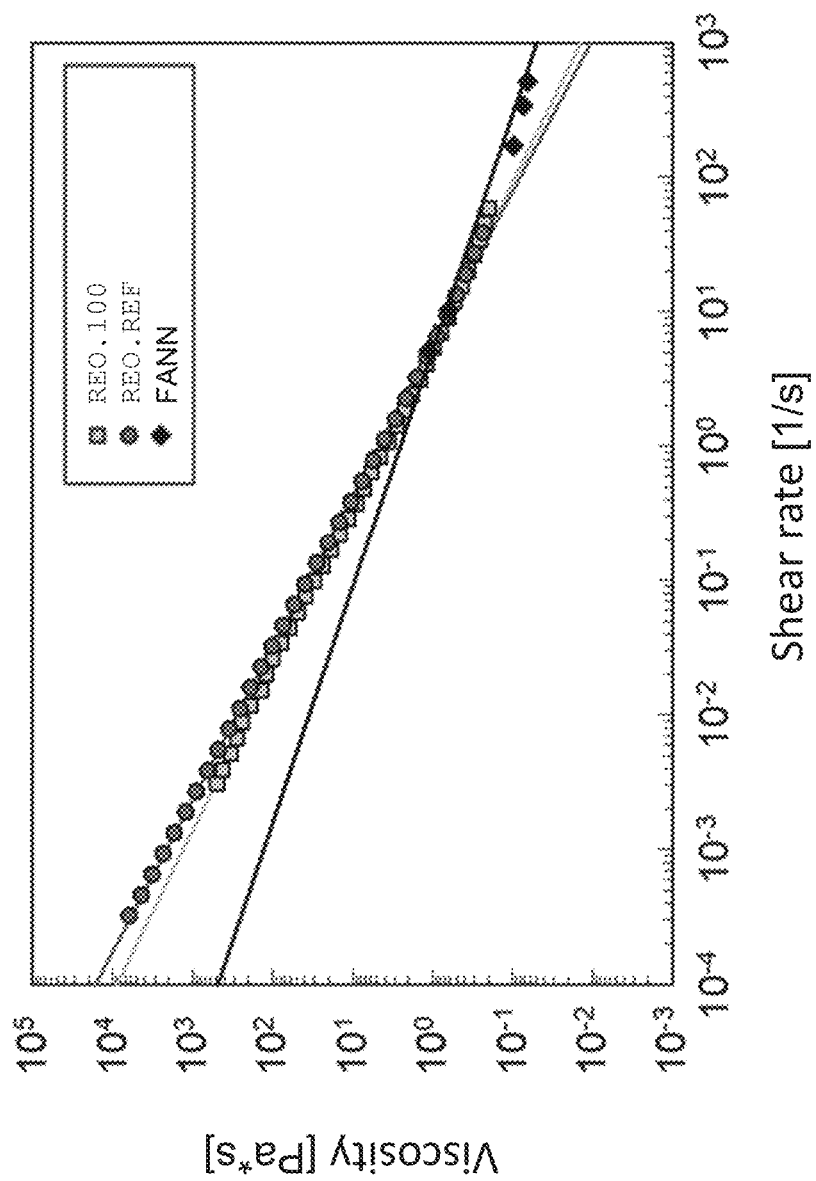
FIG. 5 is a graph showing viscosity as a function of the shear rate of a drilling mud with no cuttings, measured by means of a rheometer according to the present invention, a standard laboratory rheometer and a FANN rheometer.

By way of example, the Applicant analyzed the characteristics of a drilling mud with no cuttings at 50° C. by using the following instruments:

a laboratory rheometer, used as a reference (indicated as REO.REF in FIG. 5);

a rheometer 100 according to the present invention (indicated as REO.100 in FIG. 5); and a FANN35 rheometer, hereafter referred to as "FANN rheometer", manufactured by Fann Instrument Company (indicated as FANN in FIG. 5).

In particular, the rheometer 100 used in this comparison had the following geometric characteristics:

rotor 110 with a cylindrical twin helix 112 having:

an inside radius Ri of 4 mm and an outside radius Re of 16 mm;

a total length L of 92 mm;

an end with a tip angle α of 127.87°;

stator 130 having a radius Rs of 21 mm and a total length of 120 mm;

wherein the drilling mud reaches a maximum level of 110 mm when the rotor 110 is inserted, at least partially, inside the stator 130.

In particular, the rotor 110 that was used for this comparison had:

calibration parameter in rotation at controlled shear rate "$C_{sr}$" of 0.25915 min/s;

calibration parameter in rotation with controlled shear stress "$C_{ss}$" of 0.32922 min/s;

It should be noted that, by changing the geometric characteristics of the cylindrical twin helix 112, it is possible to obtain a different calibration parameter in rotation at controlled shear rate "$C_{SR}$" and a different calibration parameter in rotation with controlled shear stress "$C_{SS}$" than those indicated above.

For this comparison, the FANN rheometer used a rotor having the following characteristics:

rotor length 3.8 cm;

rotor radius 1.7245 cm.

The cylindrical stator coupled to the rotor of the FANN35 rheometer had the following characteristics:

stator radius 1.8415 cm;

height greater than 3.8 cm, e.g. 6 cm.

Note that this creates a gap ("shear gap, in Annulus") of 0.117 cm between the rotor and the stator of the FANN35 rheometer.

As shown in FIG. 5, the analyzed drilling mud being the same, the rheometer 100 according to the present invention has better precision than the FANN rheometer. Furthermore, advantageously, the rheometer 100 permits the exploration of a broader range of shear rates compared with the FANN rheometer.

Figure 6:
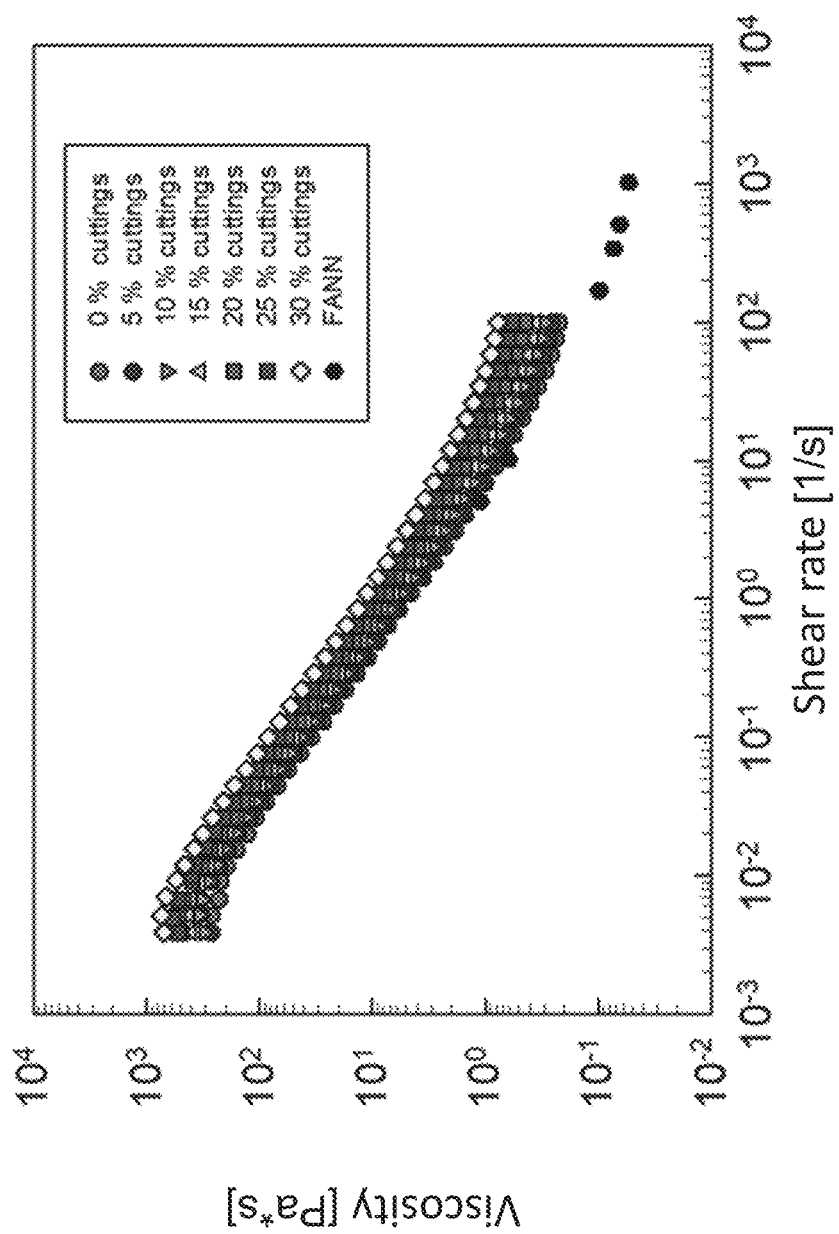
FIG. 6 is a graph showing viscosity variations as a function of the shear rate of a drilling mud as the volumetric percentage of cuttings increases, at a constant temperature of 50° C.

As shown in FIG. 6, the rheometer 100 allows, due to the rotational and convective motion caused by the cylindrical twin helix 112, taking measurements on drilling muds containing cuttings.

Preferably, such cuttings have a maximum size which is smaller than the inside radius Ri of the cylindrical twin helix 112 (e.g. considering the above-described example, it is possible to measure drilling muds having a size smaller than 4 mm).

Preferably, such cuttings have a maximum size that is smaller than the difference between the inside radius Rs of the stator 130 and the outside radius Re of the cylindrical twin helix 112.

Preferably, the maximum size of the cuttings contained in the drilling mud is equal to or smaller than half the inside radius Ri of the cylindrical twin helix 112.

Preferably, the diameter of such cuttings is smaller than or equal to the difference between the inside radius Rs of the stator 130 and the outside radius Re of the cylindrical twin helix 112.

For example, considering the above-described exemplary rheometer 100 and assuming to analyze the characteristic of a drilling mud containing a volumetric percentage of cuttings of 0% to 30%, it is possible to obtain the viscosity variation as a function of the shear rate of a drilling mud as the volumetric percentage of cuttings increases, at a constant temperature of 50° C.

The Applicant points out that such a measurement cannot be taken by using rheometers equipped with a rotor having a known geometric shape (e.g. a standard cylindrical rotor).

The Applicant also underlines that the values indicated above with reference to the geometry of the cylindrical twin helix 112 and the corresponding calibration parameters constitute merely an example of application of the present invention. In fact, the characteristic parameters of the rheometer 100 may be changed, within the limits set out in the above description and in the appended claims, to extend the rheologic characterization even to dispersions having particle sizes in excess of 2 mm.

What is claimed is:

1. A method for measuring viscosity of a drilling mud, the method comprising:
providing a rheometer, including: a rotor comprising a rotary shaft and at least two screws extending longitudinally along a first portion of said shaft; a motor coupled to said shaft and adapted to rotatably drive said rotor; a stator having a cylindrical shape; wherein said at least two screws form a cylindrical twin helix; wherein said cylindrical twin helix has an inside radius of 2 mm to 10 mm and an outside radius of 10 mm to 20 mm; wherein said stator has an inside radius which is 31% longer than the outside radius of said cylindrical twin helix;
feeding the stator with a drilling mud, said drilling mud comprising cuttings;
activating the motor for rotating the cylindrical twin helix so as to stir the drilling mud;
measuring the viscosity of the drilling mud during stirring.

2. The method according to claim 1, comprising causing a rotational and convective motion of the drilling mud in the stator by stirring the drilling mud by means of the cylindrical twin helix.

3. The method according to claim 2, wherein the rotational and convective motion prevents the cuttings included in the drilling mud from sedimenting.

4. The method according to claim 1, wherein said at least two screws are mutually congruent.

5. The method according to claim 1, wherein said shaft has a pointed end; wherein said end has a tip angle of 120° to 140°.

6. The method according to claim 1, wherein said cylindrical twin helix extends longitudinally over a length of 80 mm to 120 mm.

7. The method according to claim 1, wherein said cylindrical twin helix has a pitch that equals its length.

8. The method according to claim 1, wherein said shaft has a second portion, along which said two screws do not longitudinally extend, wherein the first portion has a radius smaller than the second portion.

9. The method according to claim 1, wherein said stator is a cylindrical container, the method comprising providing the cylindrical container with an insulating sleeve associated with a temperature control and recirculation system.

10. The method according to claim 1, wherein the cuttings have a maximum size which is smaller than the inside radius of the twin helix.

11. The method according to claim 1, wherein the cuttings have a maximum size of 4 mm.

* * * * *